United States Patent [19]
Parris

[11] Patent Number: 5,739,036
[45] Date of Patent: Apr. 14, 1998

[54] METHOD FOR ANALYSIS

[75] Inventor: Norman Alfred Parris, Hockessin, Del.

[73] Assignee: Dade International Inc., Deerfield, Ill.

[21] Appl. No.: 912,623

[22] Filed: Aug. 15, 1997

Related U.S. Application Data

[63] Continuation of Ser. No. 632,222, Apr. 15, 1996, abandoned.
[51] Int. Cl.⁶ .................................................. G01N 35/08
[52] U.S. Cl. .................. 436/53; 436/52; 422/68.1; 204/409; 204/416; 205/775; 205/789
[58] Field of Search .................. 422/68.1, 76, 77, 422/82.01, 82.04, 81–82; 436/52, 53, 163; 204/409, 416, 418, 419; 205/775, 789, 789.5

[56] References Cited

U.S. PATENT DOCUMENTS

| | | |
|---|---|---|
| 3,479,141 | 11/1969 | Smythe et al. |
| 5,149,658 | 9/1992 | Cassaday et al. ............ 436/53 |
| 5,192,504 | 3/1993 | Cassaday .................... 422/64 |
| 5,200,052 | 4/1993 | Ishibashi ..................... 204/409 |

FOREIGN PATENT DOCUMENTS

| | | |
|---|---|---|
| 0 098 550 A | 1/1984 | European Pat. Off. . |
| 0 189 316 A | 7/1986 | European Pat. Off. . |
| 0 638 809 A | 2/1995 | European Pat. Off. . |
| 89 00697 A | 1/1989 | WIPO . |
| 91 01486 A | 2/1991 | WIPO . |

*Primary Examiner*—Lyle A. Alexander
*Attorney, Agent, or Firm*—Leland K. Jordan; Lois K. Ruszala

[57] ABSTRACT

An analyzer apparatus for analyzing components of a sample has a conduit and an electrochemical sensor in the conduit. The sample is passed through the conduit using a carrier liquid that is immiscible with the sample and non-wetting of the inner wall of the conduit to reduce instabilities in the apparatus due to undue fluid movement.

6 Claims, 1 Drawing Sheet

METHOD FOR ANALYSIS

This is a continuation of application Ser. No. 08/632,222, filed on Apr. 15, 1996 now abandoned.

FIELD OF THE INVENTION

This invention relates to a method and apparatus for use with electrochemical or ion sensors.

BACKGROUND OF THE INVENTION

In the field of clinical diagnostics, there exists a need for reliable low cost devices for the routine quantitative determination of electrolyte and certain metabolites in physiological fluids. For this purpose, ion sensors, e.g., ion selective electrodes (ISE) baize routinely been applied in the clinical measurement of various electrolytes, e.g., sodium, potassium, chloride and carbonate ions and certain metabolites such as creatinine, glucose urea and the like. Enzymes are used with the ion sensors for the detection of metabolites. Such sensors consist of an electrochemical sensor with an immobilized enzyme in close contact with or continuous to electrodes for responding to the presence of the sensed metabolite.

Such biosensors are typically used in commercially available automatic analyzers. In analyzers of this general type, a series of aqueous liquid samples are processed as a flowing stream which conveys the samples via flowthrough ion sensors. The samples, calibration fluids and flushing solutions are delivered to the ion selective electrodes in the analyzer by sequential pumping or aspiration. In such flow systems, to ensure accuracy, it is essential that the successive solutions do not mix. In the past this has typically been done by interspersing several air bubbles between successive liquid types, i.e., air segmentation in the liquid stream maintains the samples as separate bands. Some designs require a substantial length of tubing between the test electrodes or sensors and the points where the reagents and/or samples are introduced. Unfortunately, the total volume of air required to separate the samples and the extended length of tubing has introduced a "spongy" character to the system. This creates the need to introduce a number of time delays to allow for the fluid system to reach equilibrium prior to measurement reads at the sensor. These characteristics produce a non-robust system and, as the tubing ages or becomes contaminated, system precision deteriorates.

In U.S. Pat. No. 3,479,141 a transport system is described in which a series of aqueous liquid samples are processed as a flowing stream and a fluorinated hydrocarbon conduit is used with intersample segments of silicone oil. The silicone oil wets and adheres to the fluorinated hydrocarbon conduit, while the aqueous liquid samples do not so wet and adhere. Unfortunately, the use of silicone oil is not suitable for many ion-selective chemical sensors since the coating action over the wall of the conduit extends to the active area of the sensor, thereby preventing the aqueous liquid samples from contacting the sensor.

U.S. Pat. No. 5,268,147 relates to a fluidic system with the capability of bi-directional flow and also to repeatedly reverse the flow for mixing, although the present invention is not concerned with mixing. U.S. Pat. No. '147 is concerned with the compressibility problem because it uses air to separate the various liquid samples. The patent offers no means of resolving the compressibility issues.

U.S. Pat. No. 5,192,504 describes a container constructed of material which is selectively wettable by a liquid fluorocarbon, an immiscible isolation liquid. Unfortunately, the liquid fluorocarbon by wetting the walls made of a fluorinated hydrocarbon material would separate the liquid samples from the contact with the electrodes and hence the electrochemical sensors would fail for the same reasons set forth for the '141 patent. The isolation liquid described in the patent is described as in Column 7, line 35 as "oozes" to cover all the walls.

Unfortunately, none of the prior art provides a suitable solution for the compressibility problem. This compressibility problem must be solved if sampling analysis at a high rate of speed is to be attained.

SUMMARY OF THE INVENTION

Many of these problems having to do with the separation of the liquid samples without causing compressibility problems and permitting the analysis of the samples at high rates of speed are solved by this invention. This invention describes an analysis apparatus for analyzing components of a liquid sample comprising a conduit having an inner wall, an inlet and an outlet, an electrochemical sensor having electrodes continuous to the inner wall of the conduit, measuring means connected to the electrodes, means to pass plural liquids, a sample and a carrier liquid successively through the conduit, the carrier liquid being immiscible with the sample, non-wetting of the inner wall of the conduit, and having a viscosity less than about 8 cs thereby to permit the liquid to reach equilibrium quickly during measuring and the samples to contact the electrodes. Preferably, the carrier liquid is a fluorocarbon and has a density of greater than 1.5 $cm^2$. Furthermore, the carrier liquid preferably has a solubility in water of less than about 10 ppm.

In a preferred embodiment, the carrier liquid is a fluorocarbon. Thus, using such a carrier liquid, the chemical analyzer becomes resilient and able to operate at high rates of speed with relatively low equilibration time, i.e., the time required for the system to stabilize its operation. These liquid fluorocarbons, being invisible with the liquid samples and non-wetting of the conduit inner walls, have no adverse effect on the lifetime or performance of either the ion-selective electrodes or the metabolite sensors.

BRIEF DESCRIPTION OF THE DRAWING

These and other features and advantages of this invention will be apparent from the following specification taken in conjunction with the accompanying drawing which the sole figure is a diagrammatic representation of a conduit used in a chemical analyzer system using ion-selective electrodes.

BRIEF DESCRIPTION OF THE PREFERRED EMBODIMENT

Figure 1:
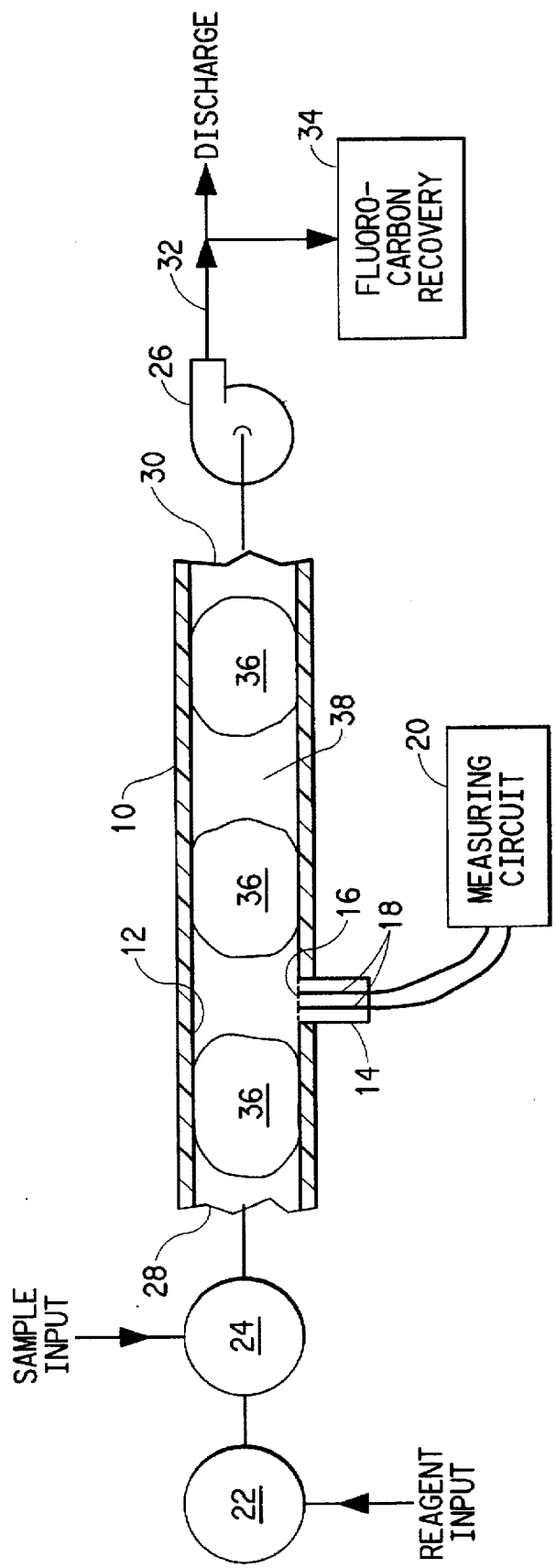

It will be seen in FIG. 1 in a typical analysis apparatus such as, for example the Dimension® XL clinical analyzer. This apparatus includes a suitable tubing or conduit 10 typically made of any suitable inert plastics such as a halo-buyl rubber, Tygon®, a plasticized form of polyvinyl chloride or C-Flex®, an ethylene butylene styrene block copolymer. The tubing or conduit is seen to have an inner wall 12 and an electrochemical sensor 14 having an enzyme electrode 18 or other standard ion-selective electrode 14 positioned in the wall of the conduit 10. The electrochemical sensor is seen to have a ion-selective membrane either attached to or immobilized in the sensor itself. The integrated electrochemical sensor 14 has a pair of enzyme electrodes 18 which are closely adjacent to the membranes 16 thus to sense the ions permitted to pass through the membranes 16. The electrodes 18 communicate with the measuring circuit 20 which typically is amperometric sensing circuit. For the detection of electrolytes, potentiometric circuitry is used. This, as is known, relies on one measuring sensor positioned in contact with a single measuring electrode and a relatively remote reference electrode.

Samples to be analyzed are introduced through appropriate valves 22, 24 respectively. They are then passed or drawn through the conduit 10 by the action of a suitable peristaltic pump 26 which is connected to the outlet of the conduit 10. The outlet 30 of the conduit 10 is connected to the peristaltic pump 26, thence to a suitable discharge line 32 which also may pass if desired to a fluorocarbon recovery chamber 34. This may consist of nothing more than a settling chamber similar to a septic system to allow the relatively dense fluorocarbon to settle out from the carrier liquid.

In accordance with this invention, the liquid samples 36 are introduced in sequence into the conduit 10 and separated by liquid fluorocarbons 38 so that they don't improperly mix and contaminate each other or mix with flush liquids or calibration standards. Liquid fluorocarbons are selected to be relatively inert and typically have a water solubility of less than 10 ppm. Their density lies in the range of 1.68–2.03 g/cm$^2$ so that droplets settle rapidly in water.

Fluorocarbons having a viscosity between 0.8 cs and 8 cs (centistokes) are usable. One such fluorocarbon sold under the name Fluorinert FC-40 having a viscosity of 2.2 cs worked adequately. A few droplets did break up occasionally but this did not seem to affect the accuracy of the sensors.

Another fluorocarbon Krytox® GPL 100 (DuPont, viscosity 8 cs) produced more severe droplet break-up which required slower pumping of the carrier liquid, thus offsetting the ability to move liquids rapidly.

As used herein, the term "wetting" means that a particular liquid with respect to a particular surface adheres to such surface. The adhesion forces between the liquid and the surface are greater than the cohesion forces of the liquid. Hence, as the liquid flows along the surface its meniscus forms an angle to the surface approaching 0°. The term "non-wetting" means that a particular liquid with respect to a particular surface does not adhere to such surface. The cohesive forces of the liquid are stronger than the adhesion forces between the liquid and the surface. Hence, as the liquid flows along the surface, its meniscus forms an angle to the surface greater than 90°. The carrier liquid used in this invention is non-wetting. The coadhesive forces of liquid fluorocarbons are known to be relatively weak, thus the systems described here show exceedingly weak interactions with the wall of the conduit.

In operation, the liquid samples 36 are able to contact and wet the inner walls 12 of the conduit 10 such that ions to be sensed can pass through the membranes 16 and be sensed by the electrodes 18. On the other hand, the carrier liquid 38 is immiscible with the liquid samples and does not cause their breakup and further is non-wetting of the conduit walls and hence does not interfere with the liquid sample in contact with the inner walls of the conduit. Since the fluorocarbons are essentially incompressible at the pressures used in the conduit, they avoid the "spongy" problems associated with air separation of the liquid samples. The analyzers may now operate at higher rates of speed.

I claim:

1. A method of analyzing components of a sample using an analysis apparatus in which the samples are passed sequentially as a flowing stream through the analysis apparatus, the analysis apparatus having an electrochemical sensor for analyzing such samples, said method comprising:

placing the liquid samples in a carrier liquid for passage through the analyzer apparatus, each sample being spaced apart by carrier liquid, the carrier liquid being a fluorocarbon and immiscible with the sample thereby to permit the carrier liquid and liquid samples to reach equilibrium during measurement.

2. The method set forth in claim 1 wherein the carrier liquid is a fluorocarbon.

3. The method set forth in claim 1 wherein the carrier liquid has a density greater than 1.5 g/cm2.

4. The method set forth in claim 1 wherein the carrier liquid has a solubility in water of less than 10 ppm.

5. The method set forth in claim 1 wherein the liquid samples and carrier liquid are passed through a conduit having an inner wall passage through the analysis apparatus, the carrier liquid being non-wetting of the inner wall of the conduit.

6. The method of claim 1 wherein the carrier liquid has a viscosity less than about 8 centistokes.

* * * * *

UNITED STATES PATENT AND TRADEMARK OFFICE
CERTIFICATE OF CORRECTION

PATENT NO. : 5,739,036
DATED : April 14, 1998
INVENTOR(S) : Norman Alfred Parris It is certified that error appears in the above-identified patent and that said Letters Patent is hereby corrected as shown below:

Column 1, Line 15: Delete "baize" and insert --have--.

Signed and Sealed this

Thirteenth Day of October 1998

Attest:

BRUCE LEHMAN

Attesting Officer

Commissioner of Patents and Trademarks